(12) United States Patent
Kennedy et al.

(10) Patent No.: US 10,285,575 B2
(45) Date of Patent: May 14, 2019

(54) ENDOSCOPIC ACCESS SYSTEM HAVING A DETACHABLE HANDLE

(71) Applicant: COOK MEDICAL TECHNOLOGIES LLC, Bloomington, IN (US)

(72) Inventors: Kenneth C. Kennedy, Clemmons, NC (US); Darach McGrath, Co. Tipperary (IE)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 473 days.

(21) Appl. No.: 13/793,434

(22) Filed: Mar. 11, 2013

(65) Prior Publication Data

US 2014/0005478 A1     Jan. 2, 2014

Related U.S. Application Data

(60) Provisional application No. 61/667,195, filed on Jul. 2, 2012.

(51) Int. Cl.
 *A61B 1/00* (2006.01)
 *A61B 1/012* (2006.01)
 (Continued)

(52) U.S. Cl.
 CPC .......... *A61B 1/012* (2013.01); *A61B 1/00066* (2013.01); *A61B 10/04* (2013.01);
 (Continued)

(58) Field of Classification Search
 CPC ..... A61B 10/02; A61B 10/06; A61B 1/00121; A61B 1/0014; A61B 1/00105; A61B 1/0125
 (Continued)

(56) References Cited

U.S. PATENT DOCUMENTS 5,137,288 A     8/1992  Starkey et al.
5,893,712 A *   4/1999  Stone et al. ............... 433/29
(Continued)

OTHER PUBLICATIONS

Intent to Grant for European Patent Application 13734614.4 dated Nov. 27, 2015, 31 pgs.
(Continued)

*Primary Examiner* — Alexandra L Newton
*Assistant Examiner* — Rynae Boler
(74) *Attorney, Agent, or Firm* — Brinks Gilson & Lione

(57) ABSTRACT

The present embodiments provide an endoscopic access system comprising a handle including a proximal handle segment and a distal handle segment. A sheath extends distally from the distal handle segment. A flexible cannula having proximal and distal ends and lumen extending therebetween is sized to be advanced through a lumen of the sheath. The handle has a coupled state in which the proximal handle segment is engaged to the distal handle segment, and where the flexible cannula is disposed through at least a portion of both the proximal and distal handle segments. The handle further has an uncoupled state in which the proximal handle segment is disengaged from the distal handle segment, and where the flexible cannula is disposed only through the distal handle segment.

18 Claims, 10 Drawing Sheets

(51) Int. Cl.
    *A61B 17/34*     (2006.01)
    *A61B 10/04*     (2006.01)
    *A61B 17/00*     (2006.01)
    *A61B 90/00*     (2016.01)

(52) U.S. Cl.
    CPC .... *A61B 17/3478* (2013.01); *A61B 2010/045* (2013.01); *A61B 2017/00278* (2013.01); *A61B 2017/00331* (2013.01); *A61B 2017/00469* (2013.01); *A61B 2017/3413* (2013.01); *A61B 2090/0811* (2016.02); *A61B 2090/3925* (2016.02)

(58) Field of Classification Search
    USPC ....... 600/566, 567, 463, 565, 437, 131, 121; 606/185, 264, 272
    See application file for complete search history.

(56) References Cited

U.S. PATENT DOCUMENTS

| | | | | |
|---|---|---|---|---|
| 7,198,599 | B2* | 4/2007 | Goto | A61B 18/1492 600/104 |
| 2004/0049128 | A1* | 3/2004 | Miller | A61B 10/025 600/566 |
| 2004/0260199 | A1* | 12/2004 | Hardia et al. | 600/566 |
| 2007/0106113 | A1* | 5/2007 | Ravo | A61B 1/00073 600/113 |
| 2009/0192463 | A1 | 7/2009 | Nardeo et al. | |
| 2010/0049208 | A1* | 2/2010 | Fritscher-Ravens | A61B 10/04 606/110 |
| 2010/0081965 | A1* | 4/2010 | Mugan et al. | 600/567 |
| 2010/0168787 | A1* | 7/2010 | Surti | A61B 17/29 606/205 |
| 2010/0280311 | A1* | 11/2010 | McGrath | A61B 1/00105 600/104 |
| 2012/0016191 | A1* | 1/2012 | Ito | A61B 1/00087 600/104 |

OTHER PUBLICATIONS

International Preliminary Report on Patentability for PCT/US2013/047546 dated Jan. 15, 2015, 8 pgs.
International Search Report and Written Opinion for PCT/US2013/047546 dated Sep. 25, 2013, 11 pgs.
Patent Examination Report No. 1 in Australian Application No. 2013287085 dated Apr. 4, 2016, 2 pages.

* cited by examiner

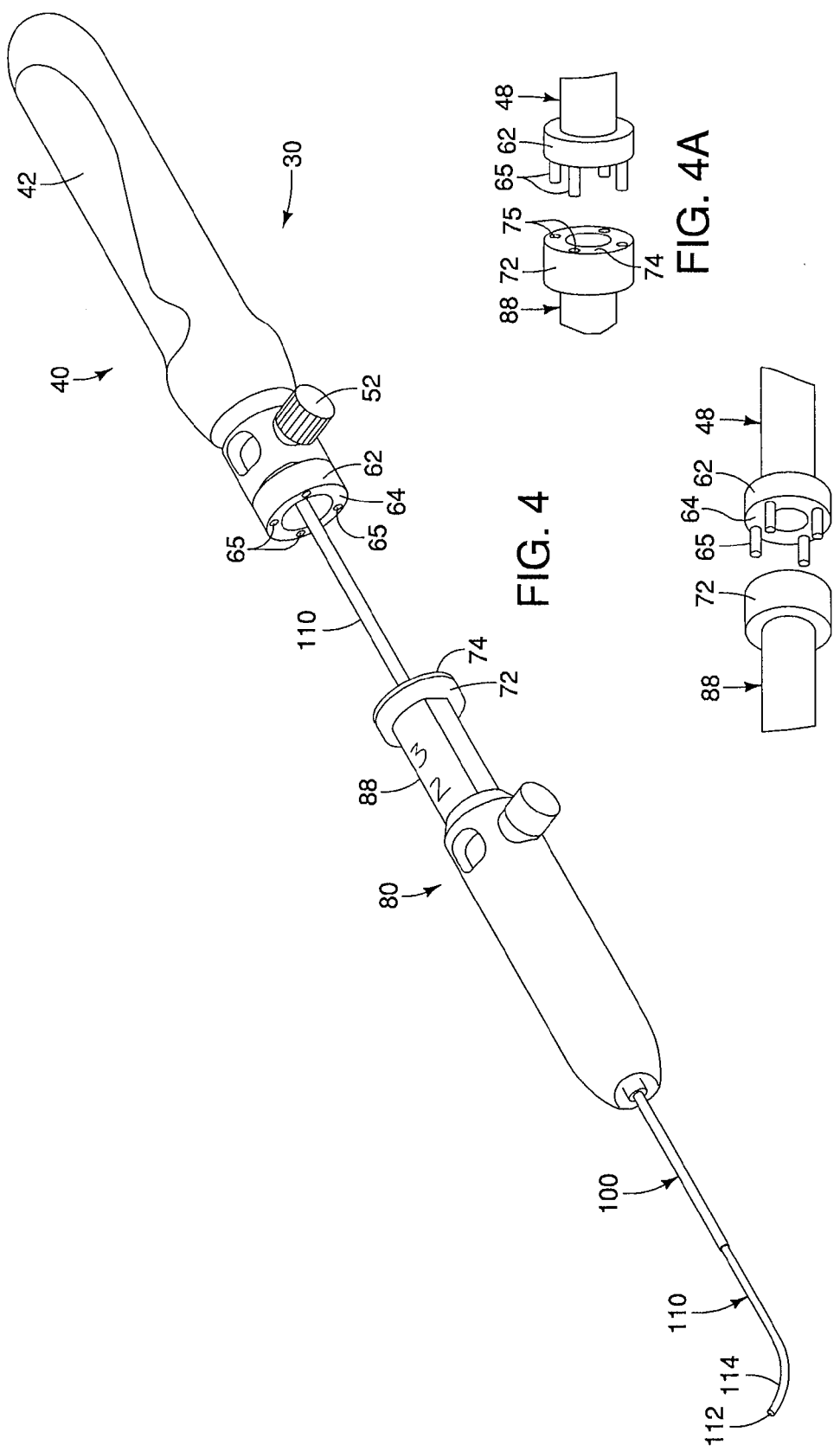

ENDOSCOPIC ACCESS SYSTEM HAVING A DETACHABLE HANDLE

PRIORITY CLAIM

This invention claims the benefit of priority of U.S. Provisional Application Ser. No. 61/667,195, entitled "Endoscopic Access System Having A Detachable Handle," filed Jul. 2, 2012, which is hereby incorporated by reference in its entirety.

BACKGROUND

The present embodiments relate generally to medical devices, and more particularly, to endoscopic access systems.

Endoscopic devices and procedures may be used to diagnose, monitor and treat various conditions by close examination of the internal organs. By way of background, a conventional endoscope generally is an instrument having a device for visualizing the interior of an internal region of a body and a lumen for inserting one or more treatment devices therethrough. A wide range of applications have been developed for the general field of endoscopes including by way of example the following: arthroscope, angioscope, bronchoscope, choledochoscope, colonoscope, cytoscope, duodenoscope, enteroscope, esophagogastro-duodenoscope (gastroscope), laparoscope, laryngoscope, nasopharyngoneproscope, sigmoidoscope, thoracoscope, and uterscope (individually and collectively, "endoscope").

In some endoscopic devices, visualization of the internal regions may be obtained using a video camera. The video camera provides a viewing field to observe the surgical instrumentation or procedure within the viewing field. Medical ultrasound has also been used to monitor a surgical procedure within a viewing field. Endoscopic ultrasound (EUS) utilizes high frequency sound waves to create an image of living tissue or an echogenic surface. Ultrasound waves are emitted from transducers located at the distal end of an endoscope. Surgical instruments having an echogenic surface reflect the ultrasound waves and enable an endoscopist to monitor the location of the device within the patient.

In some procedures, medical devices are inserted through the endoscope to access the internal organs. For example, an elongate device, such as a needle or catheter, may be inserted through an accessory channel of the endoscope. A needle may be used, by way of example, for removing tissue or cell samples, injecting a medication or diagnostic fluid, or puncturing tissue to gain access to a particular area. Fine needle aspiration (FNA) has been a well accepted method for obtaining tissue samples for pathologic or histological analysis in diagnosing a lesion, tumor neoplasm or other abnormality in internal organs. EUS and EUS-guided fine needle aspiration (EUS-FNA) have become important tools in the evaluation of tissue and cell abnormalities.

When an EUS system is used, it is important for the endoscopist to be able to maneuver the distal end of the medical device at the correct angle so that the tip is visible in the EUS plane where the ultrasound waves are emitted. Additionally, the ability to maneuver the distal end of the medical device at the correct angle may allow a physician to gain access into another duct at a particular angle, or direct subsequent medical devices in the proper direction. In many cases, however, the handle of the EUS system may limit the ability to maneuver one or more medical devices to a desired area or in a desired orientation.

SUMMARY

The present embodiments provide an endoscopic access system comprising a handle including a proximal handle segment and a distal handle segment. A sheath extends distally from the distal handle segment. A flexible cannula having proximal and distal ends and a lumen extending therebetween is sized to be advanced through a lumen of the sheath. The handle has a coupled state in which the proximal handle segment is engaged to the distal handle segment, and where the flexible cannula is disposed through at least a portion of both the proximal and distal handle segments. The handle further has an uncoupled state in which the proximal handle segment is disengaged from the distal handle segment, and where the flexible cannula is disposed only through the distal handle segment.

In one embodiment, a distal region of the proximal handle segment is releasably coupled to a proximal region of the distal handle segment, for example, using one or more interlocking elements. In an alternative embodiment, the proximal handle segment comprises adjacent first and second segments that circumferentially surround a portion of the flexible cannula in the coupled state, and the first and second segments are disengaged from one another in the uncoupled state to expose the proximal end of the flexible cannula and facilitate manipulation of the proximal end of the flexible cannula by a physician.

In yet a further alternative, the proximal handle segment comprises a slot extending axially through a gripping section of the proximal handle segment. The slot is sized to receive at least a portion of the flexible cannula in a first state, and the flexible cannula is configured to be disengaged from the slot by radial outward movement of the proximal end of the flexible cannula relative to the slot in a second state.

Advantageously, in the various embodiments herein, the proximal handle segment can be removed from an overlapping position relative to the flexible cannula, and the flexible to cannula then may be manipulated without constraints from the proximal handle segment. In particular, the proximal end of the flexible cannula may be advanced and/or rotated by a physician in any direction to cause a desired effect upon the distal end of the flexible cannula.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

Figure 1:
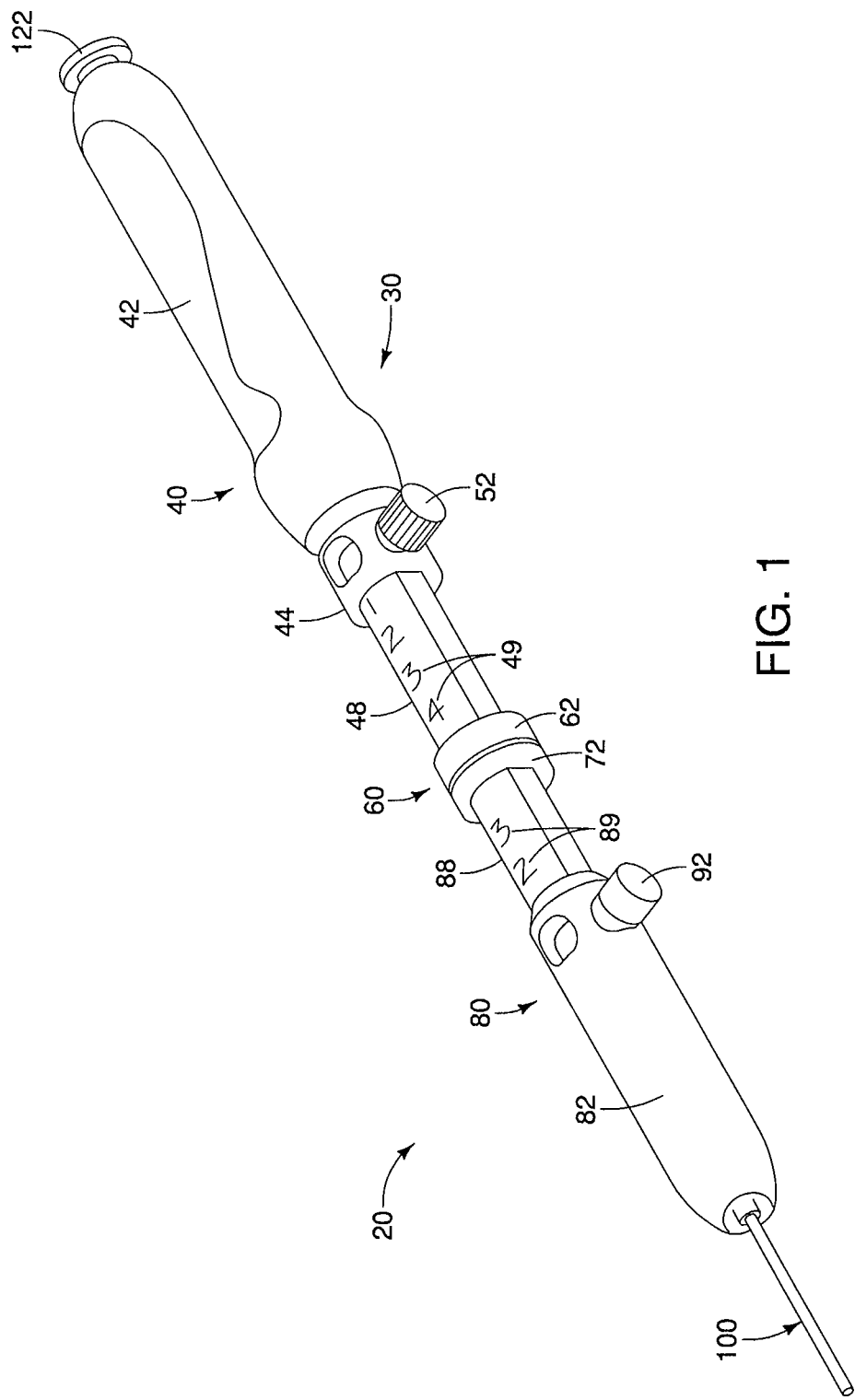
FIGS. 1-5 are perspective views illustrating an exemplary sequence of use of a first embodiment of an endoscopic access system, with FIGS. 4A-4I illustrating various exemplary couplings between proximal and distal handle segments.

In the present application, the term "proximal" refers to a direction that is generally towards a physician during a medical procedure, while the term "distal" refers to a direction that is generally towards a target site within a patent's anatomy during a medical procedure.

Referring to FIGS. 1-5, a first embodiment of an endoscopic access system 20 is described. The system 20 generally comprises a handle 30, a sheath 100 extending distally from the handle 30, an elongate flexible cannula 110, and a stylet 120.

The handle 30 comprises a proximal handle segment 40, a dividing region 60, and a distal handle segment 80. At least a portion of the proximal handle segment 40 is detachable from the distal handle segment 80, as described below in connection with FIGS. 4-5 below.

As shown in FIG. 1, the proximal handle segment 40 includes a gripping section 42 and a cannula adjuster 44. The cannula adjuster 44 is positioned distal to the gripping section 42 and is configured to identify the length of the extension of the flexible cannula 110 out of the sheath 100, as explained further in connection with FIG. 2 below. The cannula adjuster 44 may move along a proximal shaft 48 of the handle 30, and may include indicia 49 relating to the length that the flexible cannula 110 extends out of the sheath 100. A locking mechanism 52 may be used to releasably lock the cannula adjuster 44 in position. For example, the cannula adjuster 44 being positioned at 0, as depicted in FIG. 1, indicates that the flexible cannula 110 is positioned within the sheath 100 for insertion through an endoscope. By contrast, the cannula adjuster 44 being positioned at 3 or 4 indicates a predetermined amount of extension of the flexible cannula 110 beyond a distal end of the sheath 100.

The distal handle segment 80 comprises a sheath adjuster 82 that is movable over a distal shaft 88 having measurement indicia 89. A locking mechanism 92 may be used to releasably lock the sheath adjuster 82 in position relative to the distal shaft 88. The sheath adjuster 82 may be advanced proximally or distally relative to the sheath 100 when the locking mechanism 92 is disengaged, thereby allowing the sheath adjuster 82 to slide over the distal shaft 88 and relative to the sheath 100, which helps makes the system 20 compatible with a full range of endoscopes.

The distal handle segment 80 is separated from the proximal handle segment 40 by the dividing region 60. In one embodiment, a distal region 62 of the proximal handle segment 40 is releasably coupled to a proximal region 72 of the distal handle segment 80, as shown in greater detail in FIGS. 4-5 below. The distal region 62 of the proximal handle segment 40 may be formed integrally with the proximal shaft 48, while the proximal region 72 of the distal handle segment 80 may be formed integrally with the distal shaft 88, as depicted in a coupled state in FIGS. 1-3 and in an uncoupled state in FIGS. 4-5.

Figure 4C:
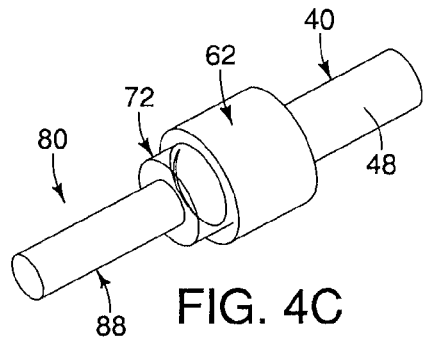
Figure 4D:
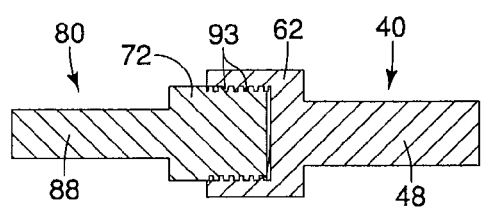
Figure 4E:
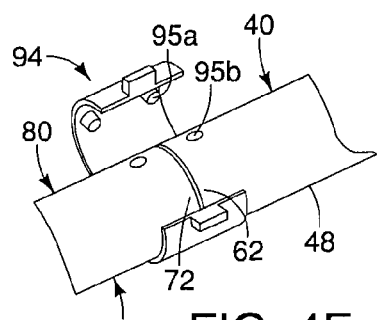
Figure 4F:
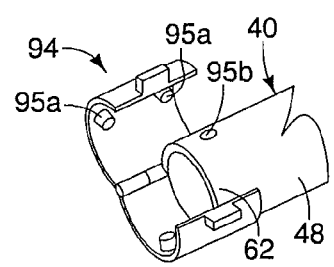
Figure 4G:
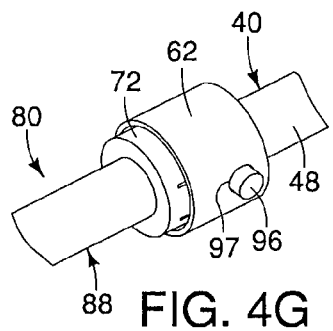
Figure 4H:
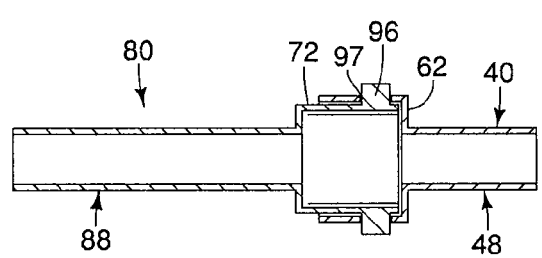
Figure 4I:
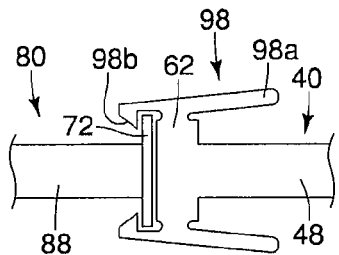
Figure 5:
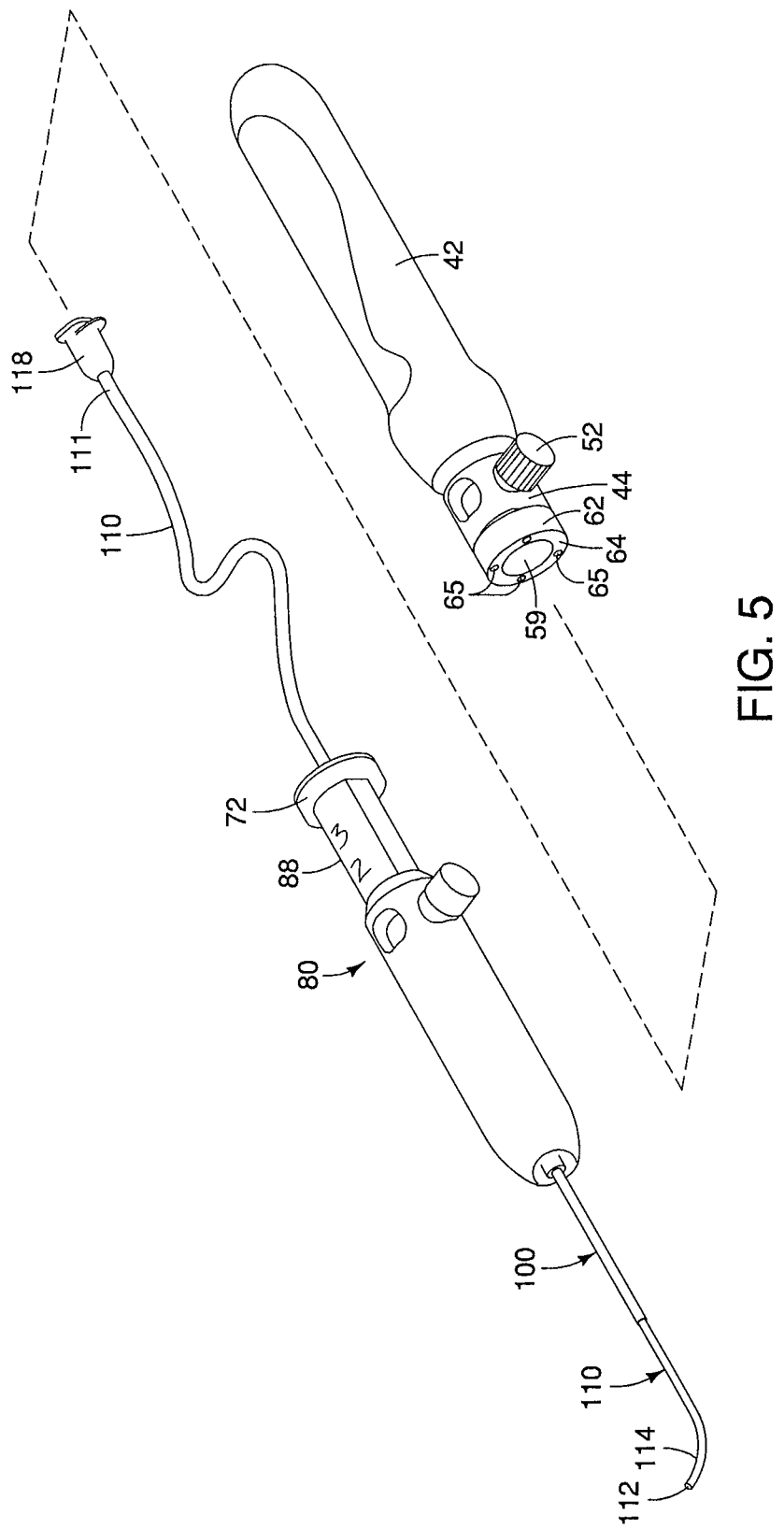

The elongate flexible cannula 110 of the system 20 includes a lumen 112 extending between a distal end 114 and a proximal end 111 of the cannula 110, as shown in FIGS. 2-5 (the proximal end 111 is best seen in FIG. 5). The flexibility of at least a portion of the elongate flexible cannula 110 preferably provides pushability and trackability sufficient to allow navigation through a body lumen or other passage without significant risk of crimping or otherwise occluding the lumen 112. In one embodiment, the elongate flexible cannula 110 may be constructed of stainless steel hypotube or a nickel-titanium alloy. As another example, one embodiment may include a polyether block amide (PEBA), PEBAX, poly-ether-ether-ketone (PEEK), ePTFE, PTFE, or PET cannula, and it will be appreciated that other polymeric materials including polymers with braided construction and/or with metallic components may also be used within the scope of this invention. This pushability and trackability will be enhanced by the removable stylet 120.

As shown in FIGS. 2A-2B, the removable stylet 120 may pass through and extend distally from the lumen 112 of the cannula 110. The stylet 120 includes a piercing tip 128, which may be provided in a lancet configuration or any number of other beveled configurations which will include any design configured for effectively piercing tissue. The tissue may be, by way of illustrative example, the exterior of a pancreatic pseudocyst, the wall of the stomach, an intestinal wall, or another artificial or natural structure between an endoscopically-accessible site and a target site, including creation of an orifice for a natural orifice translumenal endoscopic (NOTES) surgical procedure. The stylet 120 extends longitudinally through the elongate flexible cannula 110 to provide stiffness to the elongate flexible cannula 110 before piercing and/or sampling of the tissue.

The stylet 120 may include an echogenic surface, and may be made from any material known in the art. By way of example, and without limitation, materials for the stylet 120 may include stainless steel, a memory-metal alloy, such as nickel titanium, a composite, and/or similar alloys. The stylet 120 also may be constructed of and/or coated with a polymer including, for example, an echogenic polymer such as is described in PCT Pat. App. Publ. WO02/078611 to Wheatley, et al. Examples of echogenic markers on medical devices may be found in U.S. Published Application 2006/0247530, which is hereby incorporated by reference in its entirety.

In the example of FIG. 2B, a distal, dimpled echogenic region 126 of the stylet 120 is configured to reflect ultrasonic waves for generation of a visualizable image using a medical ultrasound device (e.g., external ultrasound device, endoscopic ultrasound device). In another embodiment, including one where the stylet 120 may be constructed of, or coated with an echogenic polymer, the region 126 may have a different surface configuration other than being dimpled, but most preferably presents an ultrasound-visualizable profile that provides for location and navigation of the overlying cannula 110. Additional examples of echogenic regions on a stylet and/or cannula are described in U.S. Published Application No. 2010/0160731, which is hereby incorporated by reference in its entirety.

Referring still to FIGS. 1-5, an exemplary operation of the system 20 will be described. In FIG. 1, the system 20 is provided with the handle 30 in the coupled state in which the proximal and distal handle segments 40 and 80 are coupled together via the dividing region 60. The cannula adjuster 44 is positioned at 0, as shown in FIG. 1, which indicates that the flexible cannula 110 and also the stylet 120 are positioned within the sheath 100 for insertion through an endoscope.

A distal region of the endoscope is advanced down through a bodily lumen to a target tissue site. The distal end of the endoscope is maneuvered in close proximity to the target tissue. The sheath 100 then is loaded into a proximal end of the endoscope through an accessory channel of the endoscope. The sheath 100 then is advanced until it is near the distal end of the accessory channel.

Referring to FIGS. 2A-2B, in a next step, the cannula adjuster 44 and the gripping section 42 may be advanced distally relative to the proximal shaft 48. In FIG. 2A, the cannula adjuster 44 is positioned at increment 4, indicating that the flexible cannula 110 extends a predetermined amount, and in this case the maximum amount, beyond a distal end of the sheath 100. The extension of the flexible cannula 110 beyond the distal end of the sheath 100 is shown in FIGS. 2A-2B. Additionally, the stylet 120 extends distally beyond the distal end 114 of the flexible cannula 110 at this time.

In this embodiment of FIGS. 1-5, the locking mechanism 52, e.g., a thumb screw, is part of the cannula adjuster 44 and selectively applies pressure to proximal shaft 48. A fitting 118 at a proximal end 111 of the flexible cannula 110 is initially coupled to the proximal handle 40. The proximal handle 40 can selectively move the cannula 110 forward as far as the adjuster 44.

The echogenic features of the flexible cannula 110 and/or the stylet 120, described above, allow for enhanced visualization near the target tissue site. Using such enhanced visualization, the flexible cannula 110 and the stylet 120 are advanced distally such that the lancet point of the stylet 120 pierces the target tissue in the state of FIGS. 2A-2B.

Figure 3:
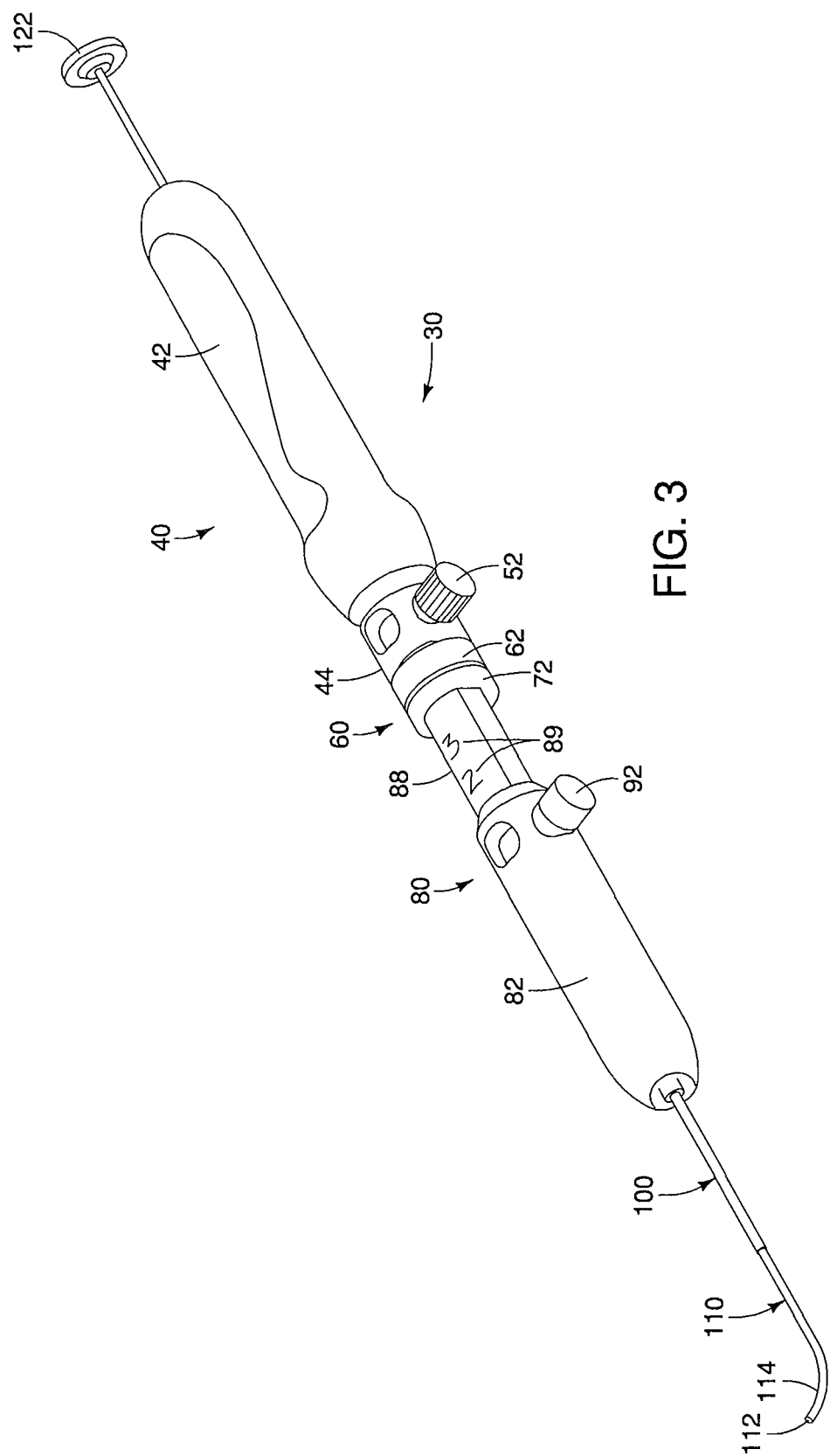

Referring now to FIG. 3, in a next step, the stylet 120 may be retracted proximally by pulling on a proximal knob 122. Upon proximal withdrawal of the stylet 120, a distal region of the flexible cannula 110 may assume a predetermined curvature, as shown in FIG. 3. In this example, the flexible cannula 110 comprises a preformed shape that forms when the relatively rigid stylet 120 is removed from within the distal region of the cannula 110. The predetermined curvature may facilitate access into a bodily passageway at a desired angle. For example, the flexible cannula 110 and/or components subsequently delivered therethrough, such as a flexible wire guide, may access an angled duct or passage with guidance from the predetermined curvature of the flexible cannula 110 and under endoscopic visualization. If desired, at this time the stylet 120 may be withdrawn entirely from the lumen 112 of the cannula 110, and from the handle 30, to allow for subsequent advancement of medical devices through the lumen 112 of the cannula 110 and/or general flexibility along the entire length of the cannula 110.

Referring to FIG. 4, in a next step, the proximal handle segment 40 is disengaged from the distal handle segment 80. Various different mechanisms may be used to allow a releasable coupling of the proximal and distal handle segments 40 and 80, as depicted in FIGS. 4A-4I. As one non-limiting example, in FIGS. 4A-4B, the distal region 62 of the proximal handle segment 40 has a distal face 64 that comprises one or more interlocking elements, such as pins 65, which correspond to one or more bores 75 on a proximal face 74 of the proximal region 72 of the distal handle segment 80. The pins 65 of the distal region 62 of the proximal handle segment 40 may be releasably coupled to the bores 75 of the proximal region 72 of the distal handle segment 80, for example, using a snap-fit connection, or other frictional engagement.

In an alternative embodiment, the distal region 62 of the proximal handle segment 40 may be releasably coupled to the proximal region 72 of the distal handle segment 80 using a magnetic arrangement, where the distal face 64 of the proximal handle segment 40 comprises a first magnetic charge and the proximal face 74 of the distal handle segment 80 comprises a second, opposing magnetic charge. In a further alternative embodiment, the distal region 62 of the proximal handle segment 40 may be releasably coupled to the proximal region 72 of the distal handle segment 80 using an adhesive or other tacking element.

In a further alternative embodiment, shown in FIGS. 4C-4D, the distal region 62 of the proximal handle segment 40 may be releasably coupled to the proximal region 72 of the distal handle segment 80 using a threaded engagement 93. In this example, the distal region 62 of the proximal handle segment 40 may be rotated relative to the proximal region 72 of the distal handle segment 80 to disengage the two segments.

In a further alternative embodiment, shown in FIGS. 4E-4F, a mechanical mechanism may be employed, such as a cover or ring 94 with one or more interlocking elements 95a that engage one or more interlocking elements 95b of the regions 62 and 72, thereby holding the proximal handle segment 40 to the distal handle segment 80 in the coupled state. The cover or ring 94 then is actuated to allow the distal region 62 of the proximal handle segment 40 to disengage from the proximal region 72 of the distal handle segment 80 in the uncoupled state. The cover or ring 94 may be disposed to at least partially circumferentially and/or axially surround an exterior part of the dividing region 60 in the coupled state.

In a further alternative of FIGS. 4G-4H, an optional actuation mechanism, such as a button 96, may be provided on the handle that causes disengagement of a mechanism holding the proximal and distal handle segments 40 and 80 adjacent to each other. In FIGS. 4G-4H, the button 96 is coupled to the proximal region 72 of the distal handle segment 80, and is disposed within a bore 97 at the distal region 62 of the proximal handle segment 40. When the button 96 is pressed radially inward beyond the perimeter of the bore 97, the proximal and distal handle segments 40 and 80 then may disengage and be moved longitudinally relative to one another.

In a further alternative of FIG. 4I, an actuating mechanism in the form of a hinge 98 is provided. The hinge 98 is generally part of the distal region 62 of the proximal handle segment 40. When a proximal end 98a of the hinge 98 is pressed radially inward, a distal end 98b of the hinge 98, which was previously constraining the proximal region 72 of the distal handle segment 80, may move radially outward to release its engagement with the proximal region 72 of the distal handle segment 80.

It will be appreciated that the releasable coupling examples are not limited to the embodiments disclosed herein, and that further devices and techniques for releasably coupling the proximal handle segment 40 to the distal handle segment 80 may be used.

Referring now to FIG. 5, in a next step, the proximal handle segment 40 can be removed from an overlapping position relative to the flexible cannula 110. In one example, a fitting 118 at a proximal end 111 of the flexible cannula 110 may be temporarily uncoupled from the cannula 110, thereby allowing the proximal handle segment 40 to be proximally retracted over the entirety of the cannula 110, as depicted in FIG. 5. In an alternative embodiment, the fitting 118 may remain coupled to the cannula 110, and the proximal handle segment 40 may comprise a channel 59 having an inner diameter that is larger than an outer diameter of the fitting 118. Alternatively, the proximal handle segment 40 can be removed from an overlapping position relative to the flexible cannula 110 using the techniques shown in the alternative embodiments of FIGS. 6-11 below.

The proximal segment 40 can be retracted over the cannula 110 and fitting 118 as illustrated by way of example the diagrams, by sliding over the device, through a full or partial gap in the handle, or separation of the handle. In exemplary embodiments, the fitting 118 extends through the entire handle.

Advantageously, once the proximal handle segment 40 is removed from an overlapping position relative to the flexible cannula 110, the flexible cannula 110 then may be manipulated without constraints from the proximal handle segment 40. In particular, in the state shown in FIG. 5, the proximal end 111 of the flexible cannula 110 may be advanced and/or rotated by a physician in any direction to cause a desired effect upon the distal end 114 of the flexible cannula 110. For example, the flexible cannula 110 may be further distally advanced into a bodily passageway upon disengagement of the proximal handle segment 40. A physician also may insert a flexible wire guide or other medical components through the fitting 118 and the lumen 112 of the flexible cannula 110 with the distal end 114 of the flexible cannula 110 in a desired location and/or orientation.

Figure 2:
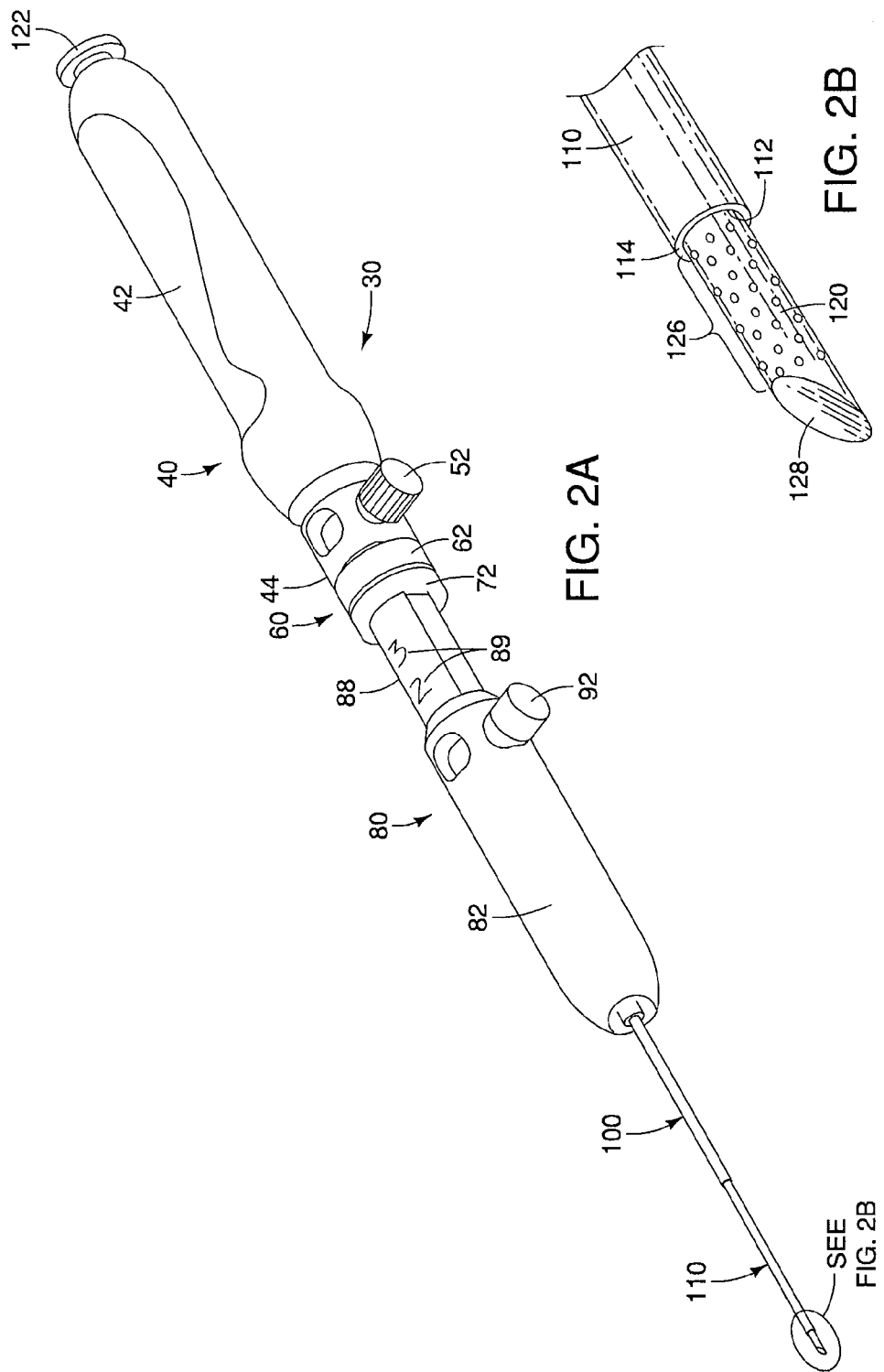

In this embodiment, only the proximal handle segment 40 is capable of gripping the flexible cannula 110 during the initial stages of the procedure described in FIGS. 1-3. Thus, upon disengagement of the proximal handle segment 40, since the flexible cannula 110 is not secured to the distal handle segment 80, the flexible cannula 110 may be freely advanced and/or rotated.

Figure 6:
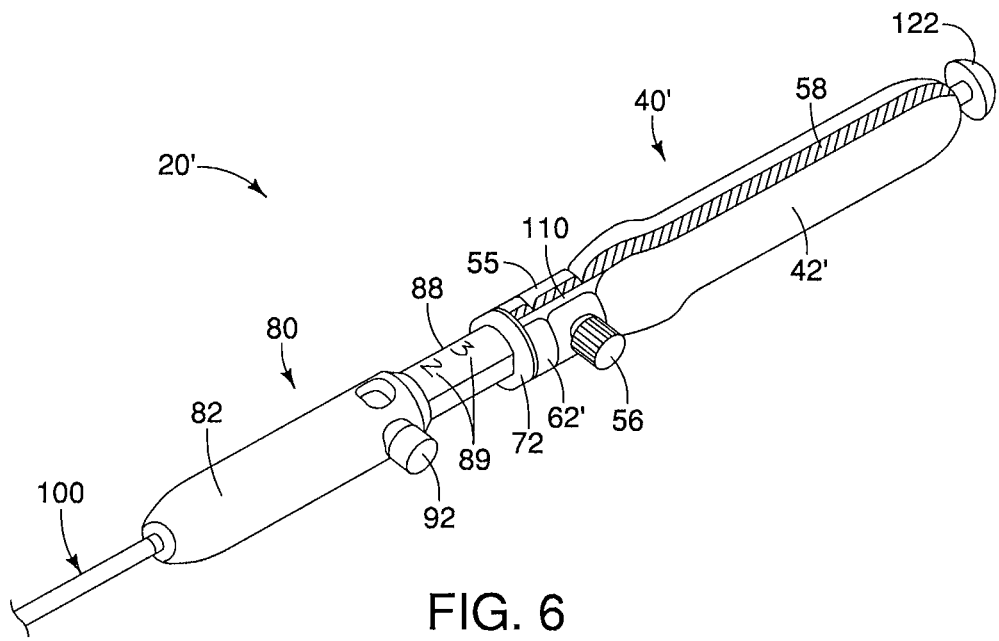
FIGS. 6-8 are perspective views illustrating an exemplary sequence of use of an alternative embodiment of an endoscopic access system.
Figure 7:
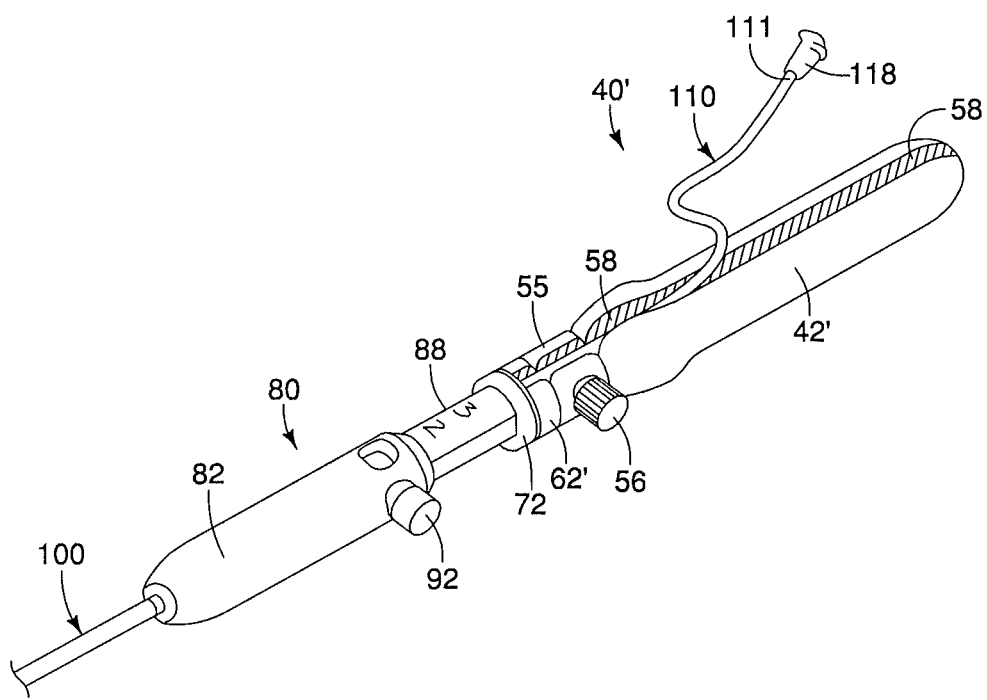
Figure 8:
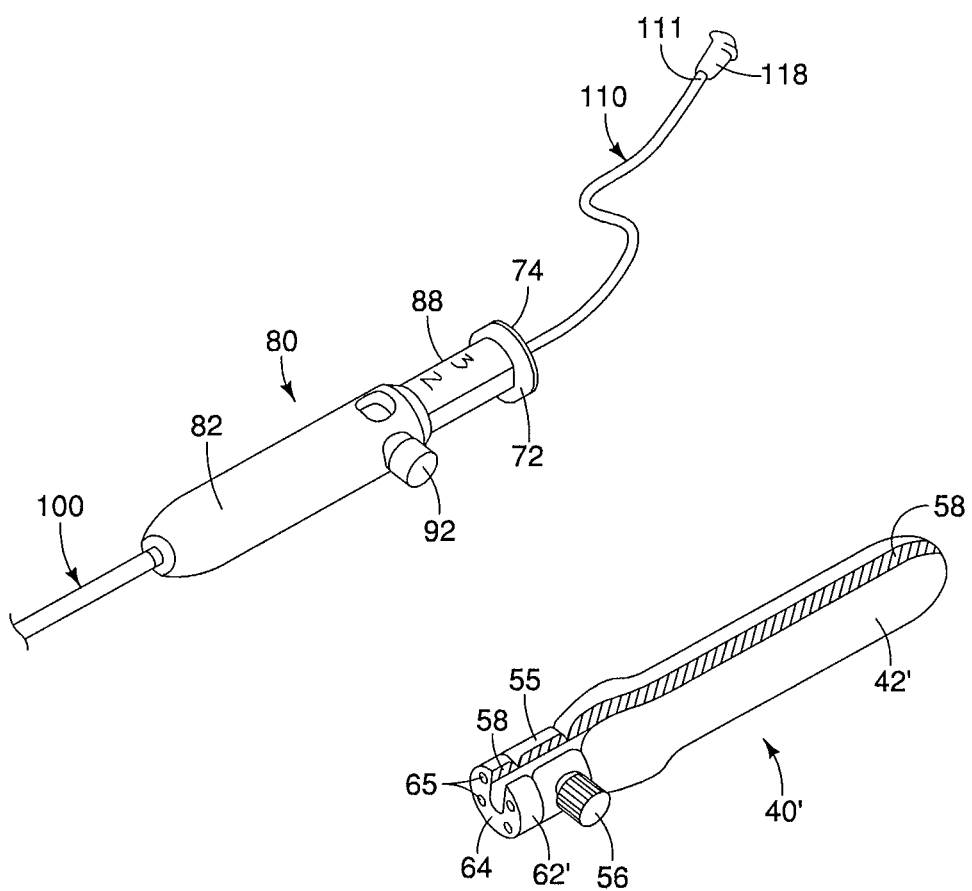

Referring now to FIGS. 6-8, an alternative ultrasound-visualizable endoscopic access system 20' is described. The alternative system 20' of FIGS. 6-8 is similar to the system 20 of FIGS. 1-5, with a main exception that an alternative proximal handle segment 40' having a slot 58 is provided. The slot 58 extends axially through a gripping section 42', through a securing section 55, and through a distal region 62'. The slot 58 is sized to receive at least a portion of the elongate flexible cannula 110, as shown in FIG. 6. One or more securing elements, such as thumb screw 56, may be coupled to the securing section 55 of the proximal handle segment 40', and may be selectively actuated to apply pressure on the flexible cannula 110 to secure the proximal handle segment 40' to the cannula 110.

Use of the alternative system 20' of FIGS. 6-8 is similar to the use of the system 20 as described in the steps of FIGS. 1-5 above. One difference is that, when a physician wishes to remove the flexible cannula 110 from an overlapping relationship with the proximal handle segment 40', the physician may apply a radial force upon the proximal end 111 of the flexible cannula 110 that is sufficient to pull the flexible cannula 110 out of engagement with the slot 58, as depicted in FIG. 7. At this time, after disengaging the securing element 56, the flexible cannula 110 then may be manipulated without constraints from the proximal handle segment 40. In particular, in the state shown in FIG. 7, the proximal end 111 of the flexible cannula 110 may be advanced and/or rotated by a physician in any direction to cause a desired effect upon the distal end 114 of the flexible cannula 110. A physician then may insert a wire guide or other medical components through the fitting 118 and the lumen 112 of the flexible cannula 110 to complete a medical procedure, as explained above. If desired, the physician may additionally disengage the proximal handle segment 40' from the distal handle segment 80, as shown in FIG. 8, using the interlocking elements 65 or other techniques described with respect to FIG. 4 above. The disengagement of the proximal handle segment 40' from the distal handle segment 80 may allow further enhanced manipulation of the proximal end 111, and in turn the distal end 114, of the flexible cannula 110.

Figure 9:
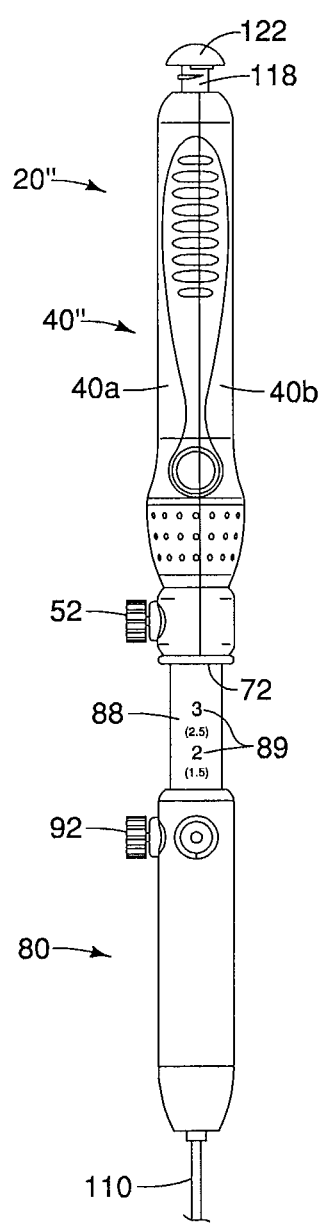
FIGS. 9-10 are top views illustrating an exemplary sequence of use of a further alternative embodiment of an endoscopic access system.
Figure 10:
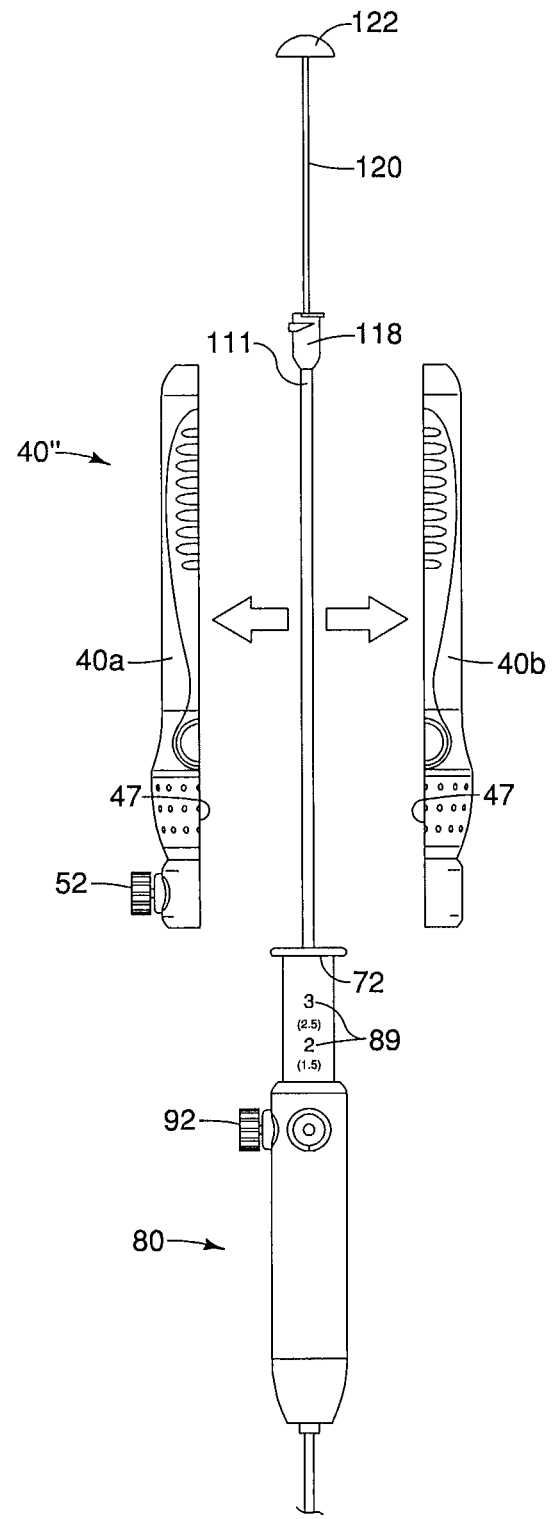

Referring now to FIGS. 9-10, an alternative ultrasound-visualizable endoscopic access system 20" is described. The alternative system 20" of FIGS. 9-10 is similar to the system 20 of FIGS. 1-5 and the system 20' of FIGS. 6-8, with a main exception that the alternative system 20" comprises an alternative proximal handle segment 40" having adjacent first and second segments 40a and 40b, which are releasably coupled to one another as shown in FIGS. 9-10. Use of the alternative system 20" of FIGS. 9-10 is similar to the use of the system 20 as described in the steps of FIGS. 1-5 above. One difference is that, when a physician wishes to remove the flexible cannula 110 from an overlapping relationship with the proximal handle segment 40", the physician may actuate the handle such that the first and second segments 40a and 40b disengage from one another. The disengagement of the first and second segments 40a and 40b of the proximal handle segment 40" may be achieved in a manner similar to disengagement of the proximal and distal handle segments 40 and 80 in FIG. 4. By way of example, and without limitation, inner surfaces 47 of the first and second segments 40a and 40b may comprises one or more interlocking elements, such as interlocking elements 65 of FIG. 4. The interlocking elements of the first segment 40a may be releasably coupled to the interlocking elements of the second segment 40b using a snap-fit connection, or other frictional engagement. For example, the physician may apply a radially outward force upon the first segment 40a and/or the second segment 40b that is sufficient to pull the first and second segments 40a and 40b out of engagement with one another, as depicted in FIG. 10. In alternative embodiments, the first and second segments 40a and 40b may be releasably coupled using a magnetic arrangement, using an adhesive or other tacking element, or a mechanical mechanism, as generally described above with respect to FIG. 4, or using other suitable mechanisms. Optionally, an actuation mechanism such as a button may be provided on the handle that causes disengagement of a mechanism holding the first and second segments 40a and 40b adjacent to each other.

Upon disengagement of the first and second segments 40a and 40b as shown in FIG. 10, the flexible cannula 110 then may be manipulated without constraints from the proximal handle segment 40". In particular, in the state shown in FIG. 10, the proximal end 111 of the flexible cannula 110 may be advanced and/or rotated by a physician in any direction to cause a desired effect upon the distal end 114 of the flexible cannula 110. A physician then may insert a wire guide or other medical components through the fitting 118 and the lumen 112 of the flexible cannula 110 to complete a medical procedure, as explained above.

Figure 11:
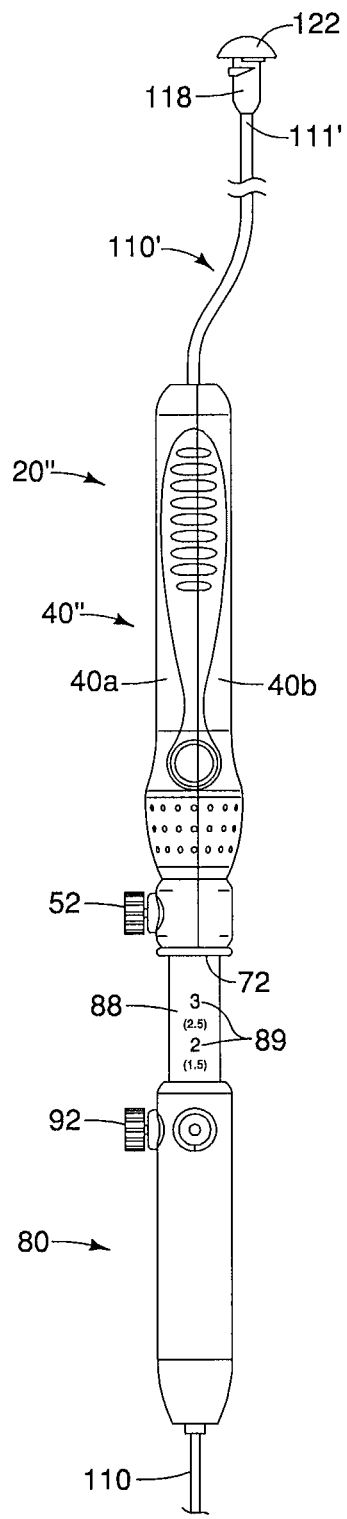
FIG. 11 is a top view illustrating features of a further alternative embodiment of an endoscopic access system.

Referring to FIG. 11, the system 20" of FIGS. 9-10 is shown having an alternative flexible cannula 110' having a greater length than the flexible cannula 110, such that a proximal end 111' of the flexible cannula 110' extends proximally beyond the handle 40" at all times. The embodiment of FIG. 11 may allow for more manipulation length to be available to the physician once the proximal handle segment 40" is disengaged, as explained in FIG. 10. Notably, the alternative flexible cannula 110' having a greater length may also be used in the embodiments of FIGS. 1-5 and FIGS. 6-8 described above.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. An endoscopic access system, comprising:
   a handle comprising a proximal handle segment and a distal handle segment;
   a sheath extending distally from the distal handle segment;
   a flexible cannula having proximal and distal ends and lumen extending therebetween, where the flexible cannula is sized to be advanced through a lumen of the sheath; and
   a stylet removably disposed through the lumen of the flexible cannula, where the sheath remains longitudinally steady relative to the distal handle segment, the cannula advances relative to the sheath, and the stylet advances relative to the sheath,
   where the handle has a coupled state in which the proximal handle segment is engaged to the distal handle segment, and the flexible cannula is disposed through at least a portion of both the proximal and distal handle segments in the coupled state, and
   where the handle has an uncoupled state in which the proximal handle segment is disengaged from the distal handle segment, and the flexible cannula is disposed only through the distal handle segment in the uncoupled state; and
   where the flexible cannula is used within a bodily passageway after the handle segments are uncoupled.

2. The system of claim 1 where a distal region of the proximal handle segment is configured to be releasably coupled to a proximal region of the distal handle segment using one or more interlocking elements.

3. The system of claim 1 where the proximal handle segment comprises adjacent first and second segments that circumferentially surround a portion of the flexible cannula in the coupled state, where the first and second segments of the proximal handle segment are disengaged from one another in the uncoupled state to expose the proximal end of the flexible cannula and permit manipulation of the proximal end of the flexible cannula.

4. The system of claim 1 where the proximal handle segment comprises a slot extending axially through a gripping section of the proximal handle segment, where the slot is sized to receive at least a portion of the flexible cannula in a first state, and where the flexible cannula is configured to be disengaged from the slot by radial outward movement of the proximal end of the flexible cannula relative to the slot in a second state.

5. The system of claim 1 where the stylet includes a piercing distal tip, a flexible body length extending proximally from the piercing distal tip, and an echogenic stylet portion disposed immediately adjacent the piercing distal tip, the echogenic stylet portion configured to provide reflection of ultrasonic waves sufficient for ultrasonic imaging of the echogenic stylet portion at a resolution providing for effective navigation the flexible cannula in a body.

6. The system of claim 1 where the proximal handle segment comprises a gripping section and a cannula adjuster movable over a proximal shaft, where advancement of the gripping section is adapted to be advanced to adjust the length of extension of the distal end of the flexible cannula out of the sheath, and where the cannula adjuster is adapted to be releasably coupled to the shaft to limit distal advancement of the gripping section and the flexible cannula.

7. A method for providing endoscopic access to a target site, the method comprising:
   providing a handle comprising a proximal handle segment and a distal handle segment, a sheath extending distally from the distal handle segment, a flexible cannula sized to be advanced through a lumen of the sheath, and a stylet removably disposed through the lumen of the flexible cannula, where the sheath remains longitudinally steady relative to the distal handle segment, the cannula advances relative to the sheath, and the stylet advances relative to the sheath,
   where the handle is provided in a coupled state in which the proximal handle segment is engaged to the distal handle segment, and the flexible cannula is disposed through at least a portion of both the proximal and distal handle segments; and
   disengaging the proximal handle segment from the distal handle segment while the sheath is inserted into a bodily passageway and the flexible cannula is inserted within the lumen of the sheath to achieve an uncoupled state, where the flexible cannula is disposed only through the distal handle segment in the uncoupled state, and
   where the flexible cannula is used within the bodily passageway after the handle segments are uncoupled.

8. The method of claim 7 further comprising manipulating a proximal end of the flexible cannula, independently of the proximal and distal handle segments, in the uncoupled state.

9. The method of claim 7 further comprising releasably coupling a distal region of the proximal handle segment to a proximal region of the distal handle segment using one or more interlocking elements.

10. The method of claim 7 where the proximal handle segment comprises adjacent first and second segments that circumferentially surround a portion of the flexible cannula in the coupled state, the method further comprising disengaging the first and second segments of the proximal handle segment from one another in the uncoupled state to expose a proximal end of the cannula and facilitate manipulation of the proximal end of the flexible cannula.

11. The method of claim 7 further comprising:
   providing a slot extending axially through a gripping section of the proximal handle segment, where the slot is sized to receive at least a portion of the flexible cannula in the coupled state; and
   disengaging the flexible cannula from the slot by radial outward movement of the proximal end of the flexible cannula relative to the slot.

12. The method of claim 7 further comprising removably disposing a stylet through a lumen of the flexible cannula.

13. The method of claim 7 where the proximal handle segment comprises a gripping section and a cannula adjuster movable over a proximal shaft, where advancement of the gripping section is adapted to be advanced to adjust the length of extension of the distal end of the flexible cannula out of the sheath, and where the cannula adjuster is adapted to be releasably coupled to the shaft to limit distal advancement of the gripping section and the flexible cannula.

14. An endoscopic access system, comprising:
   a handle comprising a proximal handle segment and a distal handle segment;
   a sheath extending distally from the distal handle segment; and a flexible cannula having proximal and distal ends and lumen extending therebetween, where the flexible cannula is sized to be advanced through a lumen of the sheath; and a stylet removably disposed through the lumen of the flexible cannula, where the sheath remains longitudinally steady relative to the distal handle segment, the cannula advances relative to the sheath, and the stylet advances relative to the sheath, where a proximal region of the flexible cannula is disposed circumferentially within the proximal and distal handle segments in a first state, and where the proximal handle segment is removed from an overlapping relationship with the flexible cannula in a second state, where the distal handle segment and the flexible cannula maintain relative axial positioning during removal of the proximal handle segment;

where the proximal handle segment is adapted to be removed to the second state while the sheath is inserted into a bodily passageway and the flexible cannula is inserted within the lumen of the sheath, and where the flexible cannula is used within the bodily passageway after the handle segments are uncoupled.

15. The system of claim 14 where the handle has a coupled state in which the proximal handle segment is engaged to the distal handle segment, where the flexible cannula is disposed through at least a portion of both the proximal and distal handle segments in the coupled state, and where the handle has an uncoupled state in which the proximal handle segment is disengaged from the distal handle segment such that the flexible cannula is disposed only through the distal handle segment in the uncoupled state.

16. The system of claim 15 where the distal region of the proximal handle segment is configured to be releasably coupled to the proximal region of the distal handle segment using one or more interlocking elements.

17. The system of claim 15 where the proximal handle segment comprises adjacent first and second segments that circumferentially surround a portion of the flexible cannula in the coupled state, where the first and second segments of the proximal handle segment are disengaged from one another in the uncoupled state to expose the proximal end of the flexible cannula and facilitate manipulation of the proximal end of the flexible cannula.

18. The system of claim 14 where the proximal handle segment comprises a slot extending axially through a gripping section of the proximal handle segment, where the slot is sized to receive at least a portion of the flexible cannula in the first state, and where the flexible cannula is configured to be disengaged from the slot by radial outward movement of the proximal end of the flexible cannula relative to the slot in the second state.

\* \* \* \* \*

UNITED STATES PATENT AND TRADEMARK OFFICE
CERTIFICATE OF CORRECTION

| | |
|---|---|
| PATENT NO. | : 10,285,575 B2 |
| APPLICATION NO. | : 13/793434 |
| DATED | : May 14, 2019 |
| INVENTOR(S) | : Kennedy et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 824 days.

Signed and Sealed this
Twenty-sixth Day of May, 2020

Andrei Iancu
*Director of the United States Patent and Trademark Office*